US010068492B2

(12) United States Patent
Caskey et al.

(10) Patent No.: US 10,068,492 B2
(45) Date of Patent: Sep. 4, 2018

(54) CONTROLLED RESOURCES BASED ON GOOD BEHAVIOR

(71) Applicant: International Business Machines Corporatio, Armonk, NY (US)

(72) Inventors: Sasha P Caskey, New York, NY (US); Dimitri Kanevsky, Ossining, NY (US); Sameer Maskey, New York, NY (US); Tara N Sainath, New York, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 66 days.

(21) Appl. No.: 14/991,280

(22) Filed: Jan. 8, 2016

(65) Prior Publication Data
US 2016/0125760 A1     May 5, 2016

Related U.S. Application Data (63) Continuation of application No. 13/544,953, filed on Jul. 9, 2012, now Pat. No. 9,275,424.

(51) Int. Cl.
| | |
|---|---|
| *G09B 19/00* | (2006.01) |
| *G06Q 50/22* | (2018.01) |
| *G06Q 10/10* | (2012.01) |

(52) U.S. Cl.
CPC ......... *G09B 19/00* (2013.01); *G06Q 10/1057* (2013.01); *G06Q 50/22* (2013.01)

(58) Field of Classification Search
USPC ........................................................ 434/238
See application file for complete search history.

(56) References Cited

U.S. PATENT DOCUMENTS

| | | | |
|---|---|---|---|
| 6,591,265 B1 | 7/2003 | Erickson et al. | |
| 6,669,286 B2 | 12/2003 | Iusim | |
| 7,904,818 B2 | 3/2011 | Lauridsen et al. | |
| 7,958,234 B2 | 6/2011 | Thomas et al. | |
| 2007/0130323 A1 | 6/2007 | Landsman et al. | |
| 2009/0157873 A1 | 6/2009 | Kilcoyne et al. | |
| 2014/0316813 A1* | 10/2014 | Bauer ................ | G06F 19/3487 705/3 |

OTHER PUBLICATIONS

Aggarwal et al., "Human Motion: Modeling and Recognition of Actions and Interactions," Proceedings of the 2nd International Symposium on 3D Data Processing, Visualization, and Transmission 2004.

(Continued)

*Primary Examiner* — Kesha Frisby
(74) *Attorney, Agent, or Firm* — Patent Portfolio Builders PLLC (57) ABSTRACT

Computing system resources are controlled based on the behavioral attributes associated with users of the computing system. These behavioral attributes are monitored in real time and through a historical log, and behavioral attributes that fall outside pre-determined preferred behavioral parameters are detected. Access by the computing system user to computing system resources contained in a preferred and habitually accessed computing system resource set associated with the computing system user are adjusted in response to the detection of the behavioral attribute outside the pre-determined preferred behavioral parameters.

20 Claims, 2 Drawing Sheets

(56) References Cited

OTHER PUBLICATIONS

Cardinaux et al., "Video Based Technology for Ambient Assisted Living: A review of the literature," Journal of Ambient Intelligence and Smart Environments (JAISE), 2011.
David A Harding, "Workrave Fights Repetitive Strain Injuries", http://dtrt.org, 2011.
Geist, "Computer and e-mail workplace surveillance in Canada: the shift from reasonable expectation of privacy to reasonable surveillance," Canadian Bar Review, 2003.
Keller, "Monitoring employees: Eyes in the workplace," CNN.com, Jan. 2, 2001, http://archives.cnn.com/2001/CAREER/trends/01/02/surveillence/.
Veronica Pamoukaghlian, "Social Network Addiction a Scientific No Mans Land", http://brainblogger.com/2011/01/07/social-network-addiction-a-scientific-no-mans-land/, Jan. 7, 2011.

* cited by examiner

CONTROLLED RESOURCES BASED ON GOOD BEHAVIOR

CROSS-REFERENCE TO RELATED APPLICATIONS

The present application is a continuation of co-pending U.S. patent application Ser. No. 13/544,953 filed Jul. 9, 2012. The entire disclosure of that application is incorporated herein by reference.

FIELD OF THE INVENTION

The present invention relates to behavior monitoring and modification.

BACKGROUND OF THE INVENTION

Behavioral choices both at work and outside the workplace can affect the health and productivity of employees. The health and productivity of employees are important to employers and can be related to costs, for example, in terms of lost productivity and healthcare costs. Healthy employees save an employer money on health insurance premiums and lost days of productivity as illnesses and work absences result from unhealthy life style choices. For example, diabetes and heart disease have resultant costs that are paid for by patients, employers and governments. In certain situations, healthier lifestyle choices can reduce or even eliminated many of these costs. Diabetes, for example, affected 24 million in 2008, according to the CDC. This represents an increase of nearly 3 million people since 2006. That same year the disease killed approximately 72,000 people. Heart disease, which killed over 800,000 people in 2006, according to the CDC, affects about 80 million Americans and is primarily caused by poor diet and lack of exercise over a lifetime.

In an attempt to reduce these costs and to encourage healthier behavioral choices among employees, companies have developed incentive systems for living a lifestyle that is deemed healthier. For example, health rebates can be awarded for going to the gym and eating a healthy diet. Other systems have also been implemented to award good user behavior. For example, insurance companies reduce regular payments if a customer does not smoke and participates in regular exercise. For certain companies, employees contribute a portion of their own health insurance through premiums, co-pays, and deductibles. Since the 1996 Health Insurance Portability and Accountability Act, allows employers to differentiate premiums based on an employee behaviors, which can be represented, for example, by weight, blood pressure, cholesterol levels, and smoking. Incentive programs that provide rewards to employees, however, can be too expensive for companies or do not provide sufficient motivation to encourage good behavior.

Additional low costs or no cost stimulus programs are desired for encouraging healthy behavior are desired. Various methods exist to address good behavior without spending large sums of money like putting names on boards and giving symbolic, i.e., inexpensive, presents. Similar types of awards are used by parents and teachers, for example, allowing children and students to participate in fun activities as a reward for good behavior. But this kind of awards is not applicable to adults. Therefore, low or no cost incentives to encourage healthier behavioral choices in adults both at work and outside the workplace are desired.

SUMMARY OF THE INVENTION

Systems and methods in accordance with exemplary embodiment of the present invention reward good or preferred behavior by controlling access to computer and network, e.g., internet, resources available to employees. Employees demonstrating good behavior such as desired workstation ergonomics and participation in regular exercise are allocated more central processor unit (CPU) power and faster network access. These extra perks that workers receive do not result in significant additional costs to the company, because the additional resources being provided are already available within the computing system of the company. Existing resources are reallocated based on preferred or good behavior, and new resources do not have to added. In one embodiment, a visual monitoring system such as a video system observes a work station, and that data generated are user to determine if the posture of the worked in that work station includes a straight back, a keyboard located lower than the desk top and eyes directed parallel to the floor. If deviation from pre-defined preferred behavioral parameters covering worker posture is detected, then access by that use to computing system resources is adjusted or throttled. For example, the processing of user commands that involve central processing unit (CPU) and network resource usage is decreased. In addition, that worked is provided with a visual prompt, for example using a graphical user interface on the computer monitor or the user, indicating the behavioral parameters that are outside the desired ranges as well as steps to be taken to return those behavioral parameters to the desired range, e.g., by correcting posture.

This reallocation or redistribution of resources does not imposed costs on the company for additional resources or reward. Employees will adopt healthier behaviors and will be more productive at work, resulting in an improved workforce. The actions employees take to increase their resource usage could also be used during employee evaluation. Employees that are allocated less CPU and network resources would also have an associated reduction in productivity and would receive an associated lower rating. Therefore, employees are encouraged to maintain healthy behaviors through monitoring and informing users regarding these unhealthy behaviors.

In accordance with one exemplary embodiment, the present invention is directed to a method for controlling computing system resources based on behavioral attributes of users of the computing system. Real time behavioral attributes of a computing system user are monitored. Monitoring real time behavioral attributes includes monitoring current physical attributes associated with the computing system user. These current physical attributes include heart rate, respiration rate, eye movement, posture, work station ergonomics, length of time sitting, elapsed time on a given task, elapsed time since last break and combinations thereof. Monitoring of the physical attributes includes the use of video image capture devices, audio capture devices, pressure sensors, temperature sensors, biometric monitoring devices and combinations thereof. Monitoring of the real time behavioral attributes further also includes monitoring access to computing system applications, participation in computing system or network based games, access to social networking websites, access to non-work related websites and combinations thereof.

The method detects least one behavioral attribute outside pre-determined preferred behavioral parameters. In one embodiment, a log of cumulative historical behavioral attributes for the computing system user is maintained, and detecting the behavioral attribute includes detecting at least one behavioral attribute in at least one of the real time behavioral attributes and the cumulative historical behavioral attributes. These cumulative historical behavioral attributes include habitual exercise routines, preventative health care visits, adherence to prescribed medical treatments, participation in professional meetings, continuing education, work attendance record, employee evaluations, participation in charitable works, attending to family obligations, participation in civic organizations and combinations thereof.

Access by the computing system user to computing system resources contained in a preferred computing system resource set associated with the computing system user is adjusted in response to the detection of the behavioral attribute outside the pre-determined preferred behavioral parameters. The preferred computing system resource set includes a preferred and habitually accessed computing system resource set. Adjusting access by the computing system user to computing system resources includes decreasing allocation of central processor unit power, decreasing available network bandwidth and combinations thereof. In one embodiment, decreasing central processor unit power is accomplished by modifying the priority of jobs associated with the computing system user, launching additional jobs to occupy central processor unit power and combinations thereof. Adjusting access by the computing system user to computing system resources also includes denying access to computing system applications, denying access to computing system based games, denying access to websites, denying access to social media sites and combinations thereof.

In one embodiment, visual indication is provided to the computing system user regarding the behavioral attributes that are outside the pre-determined preferred behavioral parameters and regarding corrective measures to be taken to return the behavioral attributes to within the pre-determined preferred behavioral parameters. Access by the computing system user to the computing system resources is returned to pre-adjustment levels upon completion of the corrective measures by the computing system user. In one embodiment, the preferred computing system resource set associated with the computing system user is created by logging accesses to computing system applications, accesses to computing system or network based games, accesses to social networking websites and accesses to websites and determining computing system resources to include in the preferred computing system resource set based on frequency and duration of the logged accesses. When the real time behavioral attributes are maintained within the pre-determined preferred behavioral parameters, allocation of central processor unit power and available network bandwidth are increased and access to computing system applications, access to computing system based games, access to websites and access to social media sites are granted.

The present invention is also directed to a method for controlling computing system resources based on behavioral attributes of users of the computing system, by monitoring the real time behavioral attributes of each computing system user in a pre-defined team containing a plurality of computing system users. The method of claim 19, wherein the step of monitoring real time behavioral attributes further comprises monitoring comprise heart rate, respiration rate, eye movement, posture, work station ergonomics, length of time sitting, elapsed time on a given task, elapsed time since last break, access to computing system applications, participation in computing system or network based games, accesses to social networking websites, access to non-work related websites or combinations thereof. An aggregate behavioral attribute score is determined for the pre-defined team using the monitored real time behavioral attributes. In one embodiment, a log of cumulative historical behavioral attributes for each computing system user, and the log of cumulative historical behavioral attributes for each computing system user is included in the aggregate behavioral attribute score. These cumulative historical behavioral attributes include habitual exercise routines, preventative health care visits, adherence to prescribed medical treatments, participation in professional meetings, continuing education, work attendance record, employee evaluations, participation in charitable works, attending to family obligations, participation in civic organizations and combinations thereof.

The aggregate behavioral attribute score is detected as being outside pre-determined preferred behavioral parameters. Then access by all computing system users in the pre-defined team to computing system resources contained in a preferred computing system resource set associated with the pre-defined team is adjusted in response to the detection of the aggregate behavioral attribute score outside the pre-determined preferred behavioral parameters. Adjusting access by the computing system users to computing system resources includes decreasing allocation of central processor unit power, decreasing available network bandwidth, denying access to computing system applications, denying access to computing system based games, denying access to websites, denying access to social media sites and combinations thereof. In one embodiment, visual indication is provided to the computing system users regarding the aggregate behavioral attribute score outside the pre-determined preferred behavioral parameters and regarding corrective measures to be taken to return aggregate behavioral attribute score within the pre-determined preferred behavioral parameters. Access by the computing system user to the computing system resources is returned to pre-adjustment levels upon completion of the corrective measures by the computing system users.

The present invention is also directed to a computing system having a plurality of monitors to obtain data related to real time behavioral attributes of a computing system user. The plurality of monitors includes video image capture devices, audio capture devices, pressure sensors, temperature sensors, biometric monitoring devices and combinations thereof. In one embodiment, the plurality of monitors is configured to log accesses to computing system applications, participation in computing system or network based games, accesses to social networking websites, accesses to non-work related websites and combinations thereof. The data related to real time behavioral include heart rate, respiration rate, eye movement, posture, work station ergonomics, length of time sitting, elapsed time on a given task, elapsed time since last break, video data, audio data, visited websites, executed computing programs, executed computing system or networked based games, social networking websites and combinations thereof.

A monitoring module is provided in communication with the plurality of monitors to receive real time behavioral attributes data. A behavioral attribute analysis module is included in communication with the monitoring module to detect at least one behavioral attribute outside pre-determined preferred behavioral parameters based on the received real time behavioral attributed data. In one embodiment, the computing system includes a cumulative behavioral attribute module in communication with the behavioral attribute analysis module to obtain cumulative historical behavioral attributes for the computing system user. A cumulative behavioral attribute database stores a log of the cumulative historical behavioral attributes, and the behavioral attribute analysis module detects at least one behavioral attribute outside pre-determined preferred behavioral parameters based on at least one of the received real time behavioral attributed data and the log of the cumulative historical behavioral attributes. The log of cumulative historical behavioral attributes includes habitual exercise routines, preventative health care visits, adherence to prescribed medical treatments, participation in professional meetings, continuing education, work attendance record, employee evaluations, participation in charitable works, attending to family obligations, participation in civic organizations and combinations thereof.

An access control module is included in communication with the behavioral attribute analysis module and computing system resources utilized by the computing system user to adjust computing system resources contained in a preferred computing system resource set associated with the computing system user in response to an indication from the behavioral attribute analysis module regarding the detection of the behavioral attribute outside the pre-determined preferred behavioral parameters. The access control module decreases allocation of central processor unit power, decreases available network bandwidth and combinations thereof. In one embodiment, the access control module decreases central processor unit power by modifying priority of jobs associated with the computing system user, launching additional jobs to occupy central processor unit power and combinations thereof. In one embodiment, the access control module prohibits access to computing system applications, prohibits access to computing system based games, prohibits access to websites, prohibits access to social media sites and combinations thereof.

The computing system also includes a graphical user interface to provide visual indication to the computing system user of the behavioral attributes that are outside the pre-determined preferred behavioral parameters and of corrective measures to be taken to return the behavioral attributes within the pre-determined preferred behavioral parameters. In one embodiment, the behavioral attribute analysis module determines completion of the corrective measures by the computing system user, and the access control module returns access by the computing system user to the computing system resources to pre-adjustment levels upon completion of the corrective measures by the computing system user. A computing system resource access monitor is provided in communication with computing system resources to log accesses to computing system applications, accesses to computing system or network based games, accesses to social networking websites and accesses to websites by the computing system user, to identify preferred computing system resources based on frequency and duration of the logged accesses and to create the preferred computing system resource set associated with the computing system user. A preferred data resource data base in communication with the computing system resource monitor and the access control module stores the preferred computing system resource set. In one embodiment, the behavioral attribute analysis module detects when the real time behavioral attributes are maintained within the pre-determined preferred behavioral parameters, and the access control module increases allocation of central processor unit power, increases available network bandwidth, grants access to computing system applications, grants access to computing system based games, grants access to websites, grants access to social media sites and combinations thereof.

The present invention is also directed to a computing system containing a plurality of monitors to obtain data related to real time behavioral attributes of each computing system user in a pre-defined team comprising a plurality of computing system users. The plurality of monitors includes video image capture devices, audio capture devices, pressure sensors, temperature sensors, biometric monitoring devices, monitors configured to log accesses to computing system applications, monitors configured to log participation in computing system or network based games, monitors configured to log accesses to social networking websites, monitors configured to log accesses to non-work related websites combinations thereof. Data related to real time behavioral attributes include heart rate, respiration rate, eye movement, posture, work station ergonomics, length of time sitting, elapsed time on a given task, elapsed time since last break, video data, audio data, visited websites, executed computing programs, executed computing system or networked based games, social networking websites and combinations thereof.

A monitoring module in communication with the plurality of monitors receives real time behavioral attributes data. A behavioral attribute analysis module in communication with the monitoring module determines an aggregate behavioral attribute score for the pre-defined team using the received real time behavioral attribute data and to detect that the aggregate behavioral attribute score is outside pre-determined preferred behavioral parameters. In one embodiment, a cumulative behavioral attribute module in communication with the behavioral attribute analysis module obtains cumulative historical behavioral attributes for each computing system user, and a cumulative behavioral attribute database stores logs of the cumulative historical behavioral attributes. The behavioral attribute analysis module determines the aggregate behavioral attribute score for the pre-defined team further based on the log of cumulative historical behavioral attributes for each computing system and the received real time behavioral attributed. The cumulative historical behavioral attributes include habitual exercise routines, preventative health care visits, adherence to prescribed medical treatments, participation in professional meetings, continuing education, work attendance record, employee evaluations, participation in charitable works, attending to family obligations, participation in civic organizations and combinations thereof.

An access control module in communication with the behavioral attribute analysis module and computing system resources utilized by the computing system users adjusts computing system resources contained in a preferred computing system resource set associated with pre-defined team in response to an indication from the behavioral attribute analysis module regarding the detection of the aggregate behavioral attribute score outside the pre-determined preferred behavioral parameters. In one embodiment, the access control module adjusts access to computing system resources by decreasing allocation of central processor unit power, decreasing available network bandwidth, prohibiting access to computing system applications, prohibiting access to computing system based games, prohibiting access to web sites, prohibiting access to social media sites and combinations thereof. A computing system resource access monitor in communication with computing system resources logs accesses to computing system applications, accesses to computing system or network based games, accesses to social networking websites and accesses to websites by the computing system users, to identify preferred computing system resources based on frequency and duration of the logged accesses and to create the preferred computing system resource set associated with the pre-defined team. A preferred data resource database in communication with the computing system resource monitor and the access control module stores the preferred computing system resource set

DETAILED DESCRIPTION

Figure 1:
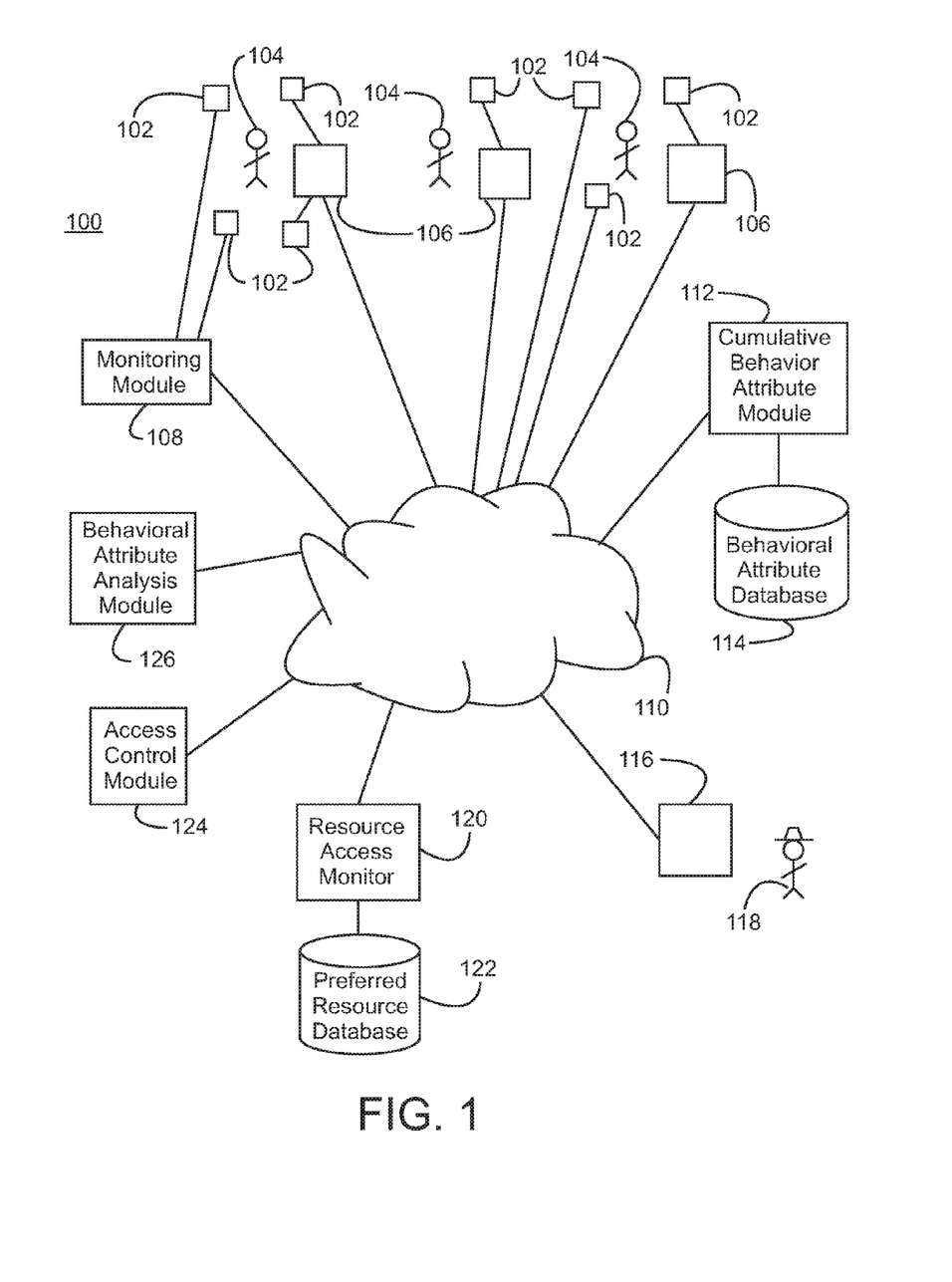
FIG. 1 is a schematic representation of an embodiment of a system for controlling resources in a computing system based on the behavioral attributes of users in accordance with the present invention.

Referring initially to FIG. 1, an exemplary embodiment of a computing system 100 for use in controlling computing system resources based on behavioral attributes is illustrated. Any suitable type of computing system can be used including, but not limited to, distributed computing systems. The computing system includes the processors, memory systems and executable computer programs required to perform the functions of the computing system in addition to the behavioral attribute monitoring and system resource control in accordance with the present invention. The computing system includes a plurality of monitors 102 that are used to obtain data related to real time behavioral attributes of one or more computing system users 104. These computing system users can be, for example, workers or employees, students, children, clients, customers, patients, military personnel or any other person utilizing a computing system. Each computing system user can be treated as an individual or as a member of a group or pre-defined team containing a plurality of computing system users for purpose of behavior monitoring and resource allocation. Examples of teams include, but are not limited to, departments within an organization and school grades or school classes.

The monitors are used to monitor and analyze the current or real time activities of a given individual or worker within an organization including physical attributes associated with the computing system user and to obtain data that describes or is otherwise associated with these activities. These data include, but are not limited to, heart rate, respiration rate, eye movement, posture, work station ergonomics, length of time sitting, elapsed time on a given task, elapsed time since last break, video data, audio data, visited websites, executed computing programs, executed computing system or networked based games, social networking websites and combinations thereof. Suitable monitors include, but are not limited to, video image capture devices, audio capture devices, pressure sensors, temperature sensors, biometric monitoring devices and combinations thereof. The monitors can also log accesses to computing system applications, participation in computing system or network based games, accesses to social networking websites, accesses to non-work related websites and combinations thereof. The monitors can also be computer equipment 106 associated with each computing system user or other hardware or software components within the computing system including servers, routers, switches, hubs, communication stacks, databases and combinations thereof. This includes software executing on hardware devices that is configured to monitor or to log the activities of users or streams of data communicated through the computing system.

The computing system includes a monitoring module 108 executing on any suitable platform within computing system. The monitoring module is in communication with the plurality of monitors and receives real time behavioral attribute data from the plurality of monitors for one or more of the users of the computing system. In embodiment, the monitors are in communication with the monitoring module through one or more networks 110, including both local area networks and wide area networks. The monitors can also be in communication with the monitoring module through the computer equipment associated with each user, e.g., a webcam on a computer, or through third party computing systems, e.g., the public switched telephone network, cellular network or security camera network. Other monitors can be directly connected to the monitoring module, i.e., not through a network. Overall, the computing system of the present invention can utilize data that monitors the current activities and conditions of the user, including the physical conditions of a user derived from any suitable data generating source as various data generating sources, e.g., security cameras, cellular phones, global positioning system components and physical access system, already exist and generate relevant data for computing system users.

In addition, to current or real-time behavioral attributes, the computing system of the present invention provides for the logging and consideration of the overall, historical behavioral attributes of computing system users. These cover behaviors occurring outside the workplace or a given location that is monitored by the computing system. In one embodiment, the computing system includes a cumulative behavioral attribute module 112 in communication with the other components and modules of the computing system across one or more networks 110. The cumulative behavior attribute module obtains cumulative historical behavioral attributes for the computing system user. These cumulative historical behavioral attributes include, but are not limited to, habitual exercise routines, preventative health care visits, adherence to prescribed medical treatments, participation in professional meetings, continuing education, work attendance record, employee evaluations, participation in charitable works, attending to family obligations, participation in civic organizations and combinations thereof. Data related to these attributes can be obtained from the computing system user, the system administrator or from a third party using any suitable method for communicating the desired data. A cumulative behavioral attribute database 114 is provided in communication with the cumulative behavioral attribute module to store a log of the cumulative historical behavioral attributes. In one embodiment, the behavioral attribute analysis module determines the aggregate behavioral attribute score for the pre-defined team further based on the log of cumulative historical behavioral attributes for each computing system and the received real time behavioral attributed.

The computing system includes a behavioral attribute analysis module 126 in communication with the other components and modules of the computing system including the monitoring module and the cumulative behavioral attribute module through one or more networks. The behavioral attribute analysis module receives and analyzes the behavioral attribute data obtained from the monitoring module and contained in the log of the cumulative historical behavioral attributes to detect at least one behavioral attribute, and potentially a plurality of behavioral attributes, outside predetermined preferred behavioral parameters. The pre-determined preferred behavioral parameters can be determined and communicated to the computing system by a computing system administrator 118 through a computing or server 116 associated with the administrator.

An access control module 124 is provided in communication with the components and modules of the computing including the behavioral attribute analysis module across one or more networks. The access control module is also in communication with computing system resources utilized by the computing system user. These including the computers 106 associated with the computing system users as well as databases, servers, switches, hubs, routers and other computing system components. This allows the access control module to adjust computing system resources available to each computing system user, including both hardware and software computing system resources. The computing system resources adjusted for a given user or groups of users are contained in a preferred and habitually accessed computing system resource set associated with a given computing system user. Access to these computing system resources, i.e., decreasing access, denying access, allowing access or increasing access is made in response to an indication from the behavioral attribute analysis module regarding the detection of the behavioral attribute outside the pre-determined preferred behavioral parameters. When a plurality of computing system users are contained with a given group or team, the behavioral attribute analysis module determines an aggregate behavioral attribute score for the pre-defined team using the received real time behavioral attribute data and the log of the cumulative historical behavioral attributes. The access control module adjusts computing system resources contained in a preferred and habitually accessed computing system resource set associated with pre-defined team in response to an indication from the behavioral attribute analysis module regarding the detection of the aggregate behavioral attribute score outside the pre-determined preferred behavioral parameters.

In one embodiment, the access control module decreases allocation of central processor unit power, decreases available network bandwidth or both. In one embodiment, the access control module decreases central processor unit power by modifying priority of jobs associated with the computing system user, launching additional jobs to occupy central processor unit power or both. In addition, the access control module prohibits access to computing system applications, prohibits access to computing system based games, prohibits access to websites, prohibits access to social media sites or combinations thereof. When the behavioral attribute analysis module detects, for example, that the real time behavioral attributes are maintained within the pre-determined preferred behavioral parameters, the access control module increases allocation of central processor unit power, increases available network bandwidth, grants access to computing system applications, grants access to computing system based games, grants access to websites, grants access to social media sites or combinations thereof.

In one embodiment, the type of resource adjustments taken by the access control module are related to the type of behavioral attribute that is outside the desired parameters and to the need or the ability of the computing system users to change the behavioral attribute either immediately or over time. For example, if a real time physical attribute is detected, e.g., failure to take a break, then the access control module can severely or rapidly decrease network access or processor power to encourage or force the user to take an immediate break. Such sever action would not be as desirable for a violation found in a historical log, as the computing system user would not be able to correct the log immediately, and extended decreases in network bandwidth or processing power inhibits the ability of the computing system user to function and therefore, the productivity of the organization. Therefore, more appropriate adjustments include the denial of access to desired social media networks or gaming applications until the behavioral attribute, e.g., getting an annual physical or meeting continuing educational requirements, has been brought within acceptable parameters.

In one embodiment, the computing system further utilizes graphical user interfaces, for example through the computer equipment associated with each computing system user, to provide visual indication to each computing system user of the behavioral attributes that are outside the pre-determined preferred behavioral parameters and of corrective measures to be taken to return the behavioral attributes within the pre-determined preferred behavioral parameters. The behavioral attribute analysis module is configured to monitor and to determine when the prescribed corrective measures have been completed by the computing system user. Once completed, and the attribute parameters brought within prescribed parameters, the access control module returns access by the computing system user to the computing system resources to pre-adjustment.

In order to determine the set of resources associated with each computing system user to be subject to adjustment, the computing system includes a computing system resource access monitor 120 in communication with computing system resources to log accesses to computing system applications, accesses to computing system or network based games, accesses to social networking websites and accesses to websites by each computing system user. In addition, habitually accessed computing system resources are identified based on frequency and duration of the logged accesses, and this information is used to create the preferred and habitually accessed computing system resource set associated with each computing system user. A preferred data resource data base 122 is provided in communication with the computing system resource monitor and the access control module to store the preferred and habitually accessed computing system resource set.

Figure 2:
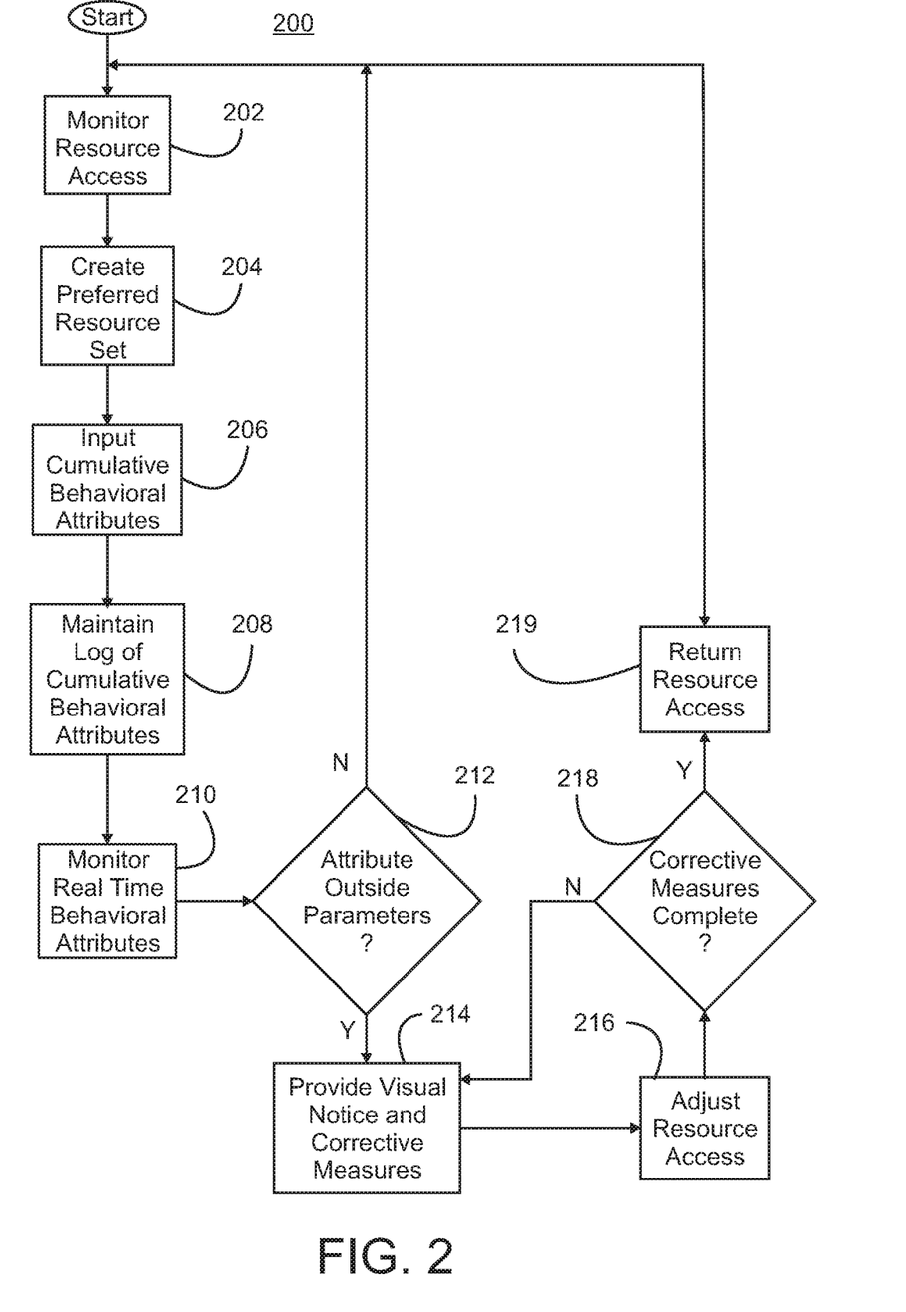
FIG. 2 is flow chart of an embodiment of a method for controlling resources in a computing system based on the behavioral attributes of users in accordance with the present invention.

Referring to FIG. 2, a method for controlling computing system resources based on behavioral attributes of users of the computing system 200 in accordance with the present invention is illustrated. Computing system resource accesses for computing system users and groups or pre-defined teams of computing system users are monitored 202. This includes logging accesses to computing system applications, accesses to computing system or network based games, accesses to social networking websites and accesses to websites. The frequency and duration with which a given computing system user accesses or uses a given computing system resource is noted and is used to create a preferred and habitually access computing system resource set 204 for each computing system user or for a team of computing system users.

Cumulative historical behavioral attributes are input 206 for each computing system user. These input cumulative historical behavioral attributes are used to create, maintain and update a log of cumulative historical behavioral attributes for each computing system user 208. Suitable cumulative historical behavioral attributes include, but are not limited to, habitual exercise routines, preventative health care visits, adherence to prescribed medical treatments, participation in professional meetings, continuing education, work attendance record, employee evaluations, participation in charitable works, attending to family obligations, participation in civic organizations or combinations thereof. In addition to historical behavioral attributes, real time behavioral attributes are monitor for each computing system user or team of computing system users 210.

Monitoring real time behavioral attributes includes monitoring current physical attributes associated with each computing system user. The current physical attributes include heart rate, respiration rate, eye movement, posture, work station ergonomics, length of time sitting, elapsed time on a given task, elapsed time since last break and combinations thereof. These physical attributes are monitored using video image capture devices, audio capture devices, pressure sensors, temperature sensors, biometric monitoring devices and combinations thereof. In addition to the physical attributes of the user, access to computing system applications, participation in computing system or network based games, access to social networking websites and access to non-work related websites are monitored in real time.

All of the log and monitored behavioral attribute data are analyzed to detecting if at least one of the real time behavioral attributes and the cumulative historical behavioral attributes is outside pre-determined preferred behavioral parameters 212 as defined, for example, by a system administrator. If all of the monitored and log attributes are within the prescribed parameters, then the monitoring of resource allocation, inputting of cumulative behavioral attributes and monitor of real time behavioral attributes continues for each computing system user or team of computing system users. In one embodiment, allocation of central processor unit power and available network bandwidth are increased in response to a determination that the real time and logged behavioral attributes are maintained within the pre-determined preferred behavioral parameters. In one embodiment, access to computing system applications, access to computing system based games, access to websites and access to social media sites are granted as a reward for maintaining real time and logged behavioral attributes within the preferred behavioral parameters.

When the monitored and logged behavioral attributes are outside the prescribed parameters, access by each computing system user to computing system resources contained in the preferred and habitually accessed computing system resource set associated with that computing system user is adjusted 216. This adjustment includes decreasing allocation of central processor unit power, decreasing available network bandwidth or both. In order to decrease central processor unit power, the priority of jobs associated with the computing system user is modified, additional jobs are launched to occupy central processor unit power or some combination of both actions are taken. In addition, access to computing system applications, access to computing system based games, access to websites or access to social media sites is denied.

In order to provide assistance to the computing system user in understanding the resource allocation adjustments and making the desired changes in their behavior attributes, visual indication is provided to each computing system user of the behavioral attributes that are outside the pre-determined preferred behavioral parameters and of corrective measures to be taken to return the behavioral attributes within the pre-determined preferred behavioral parameters 214. The computing system monitors the computing system users for completion of the communicated corrective measures and the return of behavioral attributes into compliance with the prescribed parameters 218. While the corrective measures are pending or the real-time or logged behavioral attributes remain outside the prescribed parameters, the appropriate computing system users are provided with an indication of their status and adjustments to computing system resources are maintained or are further adjusted or throttled. Once the corrective measures are completed or the behavioral attributes are brought within prescribed parameters, the access by the computing system user to the computing system resources are returned to pre-adjustment levels 219. The processes of monitoring resource access, inputting behavioral attributes and monitoring real time behavioral attributes is continued.

When real time behavioral attributes are monitored for each computing system user in a pre-defined team comprising a plurality of computing system users, an aggregate behavioral attribute score for the pre-defined team is determined using the monitored real time behavioral attributes. In addition, the aggregate behavioral attribute score for the pre-defined team includes the log of cumulative historical behavioral attributes for each computing system user. It is the aggregate behavioral attribute score that is detected outside pre-determined preferred behavioral parameters, and access by all computing system users in the pre-defined team to computing system resources contained in a preferred and habitually accessed computing system resource set associated with the pre-defined team is adjusted in response to the detection of the aggregate behavioral attribute score outside the pre-determined preferred behavioral parameters.

As will be appreciated by one skilled in the art, aspects of the present invention may be embodied as a system, method or computer program product. Accordingly, aspects of the present invention may take the form of an entirely hardware embodiment or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Methods and systems in accordance with exemplary embodiments of the present invention can take the form of an entirely hardware embodiment, an entirely software embodiment or an embodiment containing both hardware and software elements. In a preferred embodiment, the invention is implemented in software, which includes but is not limited to firmware, resident software and microcode. In addition, exemplary methods and systems can take the form of a computer program product accessible from a computer-usable or computer-readable medium providing program code for use by or in connection with a computer, logical processing unit or any instruction execution system. For the purposes of this description, a computer-usable or computer-readable medium can be any apparatus that can contain, store, communicate, propagate, or transport the program for use by or in connection with the instruction execution system, apparatus, or device. Suitable computer-usable or computer readable mediums include, but are not limited to, electronic, magnetic, optical, electromagnetic, infrared, or semiconductor systems (or apparatuses or devices) or propagation mediums. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Suitable data processing systems for storing and/or executing program code include, but are not limited to, at least one processor coupled directly or indirectly to memory elements through a system bus. The memory elements include local memory employed during actual execution of the program code, bulk storage, and cache memories, which provide temporary storage of at least some program code in order to reduce the number of times code must be retrieved from bulk storage during execution. Input/output or I/O devices, including but not limited to keyboards, displays and pointing devices, can be coupled to the system either directly or through intervening I/O controllers. Exemplary embodiments of the methods and systems in accordance with the present invention also include network adapters coupled to the system to enable the data processing system to become coupled to other data processing systems or remote printers or storage devices through intervening private or public networks. Suitable currently available types of network adapters include, but are not limited to, modems, cable modems, DSL modems, Ethernet cards and combinations thereof.

In one embodiment, the present invention is directed to a machine-readable or computer-readable medium containing a machine-executable or computer-executable code that when read by a machine or computer causes the machine or computer to perform a method for controlling computing system resources based on behavioral attributes of users of the computing system in accordance with exemplary embodiments of the present invention and to the computer-executable code itself. The machine-readable or computer-readable code can be any type of code or language capable of being read and executed by the machine or computer and can be expressed in any suitable language or syntax known and available in the art including machine languages, assembler languages, higher level languages, object oriented languages and scripting languages. The computer-executable code can be stored on any suitable storage medium or database, including databases disposed within, in communication with and accessible by computer networks utilized by systems in accordance with the present invention and can be executed on any suitable hardware platform as are known and available in the art including the control systems used to control the presentations of the present invention.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s) and steps or elements from methods in accordance with the present invention can be executed or performed in any suitable order. Therefore, it will be understood that the appended claims are intended to cover all such modifications and embodiments, which would come within the spirit and scope of the present invention.

What is claimed is:

1. A computing system for controlling computing system resources based on behavioral attributes of users of the computing system, the computing system comprising:
   a plurality of monitors to monitor real time activities of a computing system user while using the computing system and to obtain real time behavioral attributes data related to real time behavioral attributes of the computing system user, the real time behavioral attributes indicating a physical health status of the computing system user and comprising a plurality of current physical attributes and conditions of the computing system user;
   a monitoring module in communication with the plurality of monitors to receive the real time behavioral attributes data;
   a behavioral attribute analysis module in communication with the monitoring module to detect at least one behavioral attribute outside pre-determined preferred behavioral parameters based on the received real time behavioral attributes data; and
   an access control module in communication with the behavioral attribute analysis module and computing system resources utilized by the computing system user to adjust access by the computing system user to computing system resources contained in a preferred and habitually accessed computing system resource set associated with the computing system user in response to an indication from the behavioral attribute analysis module regarding the detection of the behavioral attribute outside the pre-determined preferred behavioral parameters.

2. The computing system of claim 1, wherein the plurality of monitors comprises video image capture devices, audio capture devices, pressure sensors, temperature sensors, biometric monitoring devices or combinations thereof.

3. The computing system of claim 1, wherein the plurality of monitors are configured to log accesses to computing system applications, participation in computing system or network based games, accesses to social networking websites, accesses to non-work related websites or combinations thereof.

4. The computing system of claim 1, wherein data related to real time behavioral attributes comprise heart rate, respiration rate, eye movement, posture, work station ergonomics, length of time sitting, elapsed time on a given task, elapsed time since last break, video data, audio data, visited websites, executed computing programs, executed computing system or networked based games, social networking websites or combinations thereof.

5. The computing system of claim 1, wherein:
   the computing system further comprises a cumulative behavioral attribute module in communication with the behavioral attribute analysis module to obtain cumulative historical behavioral attributes for the computing system user; and
   a cumulative behavioral attribute database to store a log of the cumulative historical behavioral attributes; and
   the behavioral attribute analysis module detects at least one behavioral attribute outside pre-determined preferred behavioral parameters based on at least one of the received real time behavioral attributed data and the log of the cumulative historical behavioral attributes.

6. The computing system of claim 5, wherein the log of cumulative historical behavioral attributes comprises habitual exercise routines, preventative health care visits, adherence to prescribed medical treatments, participation in professional meetings, continuing education, work attendance record, employee evaluations, participation in charitable works, attending to family obligations, participation in civic organizations or combinations thereof.

7. The computing system of claim 1, wherein the access control module decreases allocation of central processor unit power, decreases available network bandwidth or combinations thereof.

8. The computing system of claim 7, wherein access control module decreases central processor unit power by modifying priority of jobs associated with the computing system user, launching additional jobs to occupy central processor unit power or combinations thereof.

9. The computing system of claim 1, wherein the access control module prohibits access to computing system applications, prohibits access to computing system based games, prohibits access to websites, prohibits access to social media sites or combinations thereof.

10. The computing system of claim 1, wherein the computing system further comprises a graphical user interface to provide visual indication to the computing system user of the behavioral attributes that are outside the pre-determined preferred behavioral parameters and of corrective measures to be taken to return the behavioral attributes within the pre-determined preferred behavioral parameters.

11. The computing system of claim 10, wherein:
   the behavioral attribute analysis module determines completion of the corrective measures by the computing system user; and
   the access control module returns access by the computing system user to the computing system resources to pre-adjustment levels upon completion of the corrective measures by the computing system user.

12. The computing system of claim 1, wherein the computing system further comprises:
   computing system resource access monitor in communication with computing system resources to log accesses to computing system applications, accesses to computing system or network based games, accesses to social networking websites and accesses to websites by the computing system user, to identify habitually accessed computing system resources based on frequency and duration of the logged accesses and to create the preferred and habitually accessed computing system resource set associated with the computing system user; and a preferred data resource data base in communication with the computing system resource monitor and the access control module to store the preferred and habitually accessed computing system resource set.

13. The computing system of claim 1, wherein:

the behavioral attribute analysis module further detects when the real time behavioral attributes are maintained within the pre-determined preferred behavioral parameters; and the access control module increases allocation of central processor unit power, increases available network bandwidth, grants access to computing system applications, grants access to computing system based games, grants access to websites, grants access to social media sites or combinations thereof.

14. A computing system for controlling computing system resources based on behavioral attributes of users of the computing system, the computing system comprising:

a plurality of monitors to monitor real time activities of a computing system user while using the computing system and to obtain real time behavioral attributes data related to real time behavioral attributes of each computing system user in a pre-defined team comprising a plurality of computing system users, the real time behavioral attributes indicating a physical health status of the computing system users and comprising a plurality of current physical attributes and conditions of the system users;

a monitoring module in communication with the plurality of monitors to receive the real time behavioral attributes data;

a behavioral attribute analysis module in communication with the monitoring module to determine an aggregate behavioral attribute score for the pre-defined team using the received real time behavioral attributes data and to detect that the aggregate behavioral attribute score is outside pre-determined preferred behavioral parameters; and an access control module in communication with the behavioral attribute analysis module and computing system resources utilized by the computing system users to adjust access by all computing system users in the pre-defined team to computing system resources contained in a preferred and habitually accessed computing system resource set associated with pre-defined team in response to an indication from the behavioral attribute analysis module regarding the detection of the aggregate behavioral attribute score outside the pre-determined preferred behavioral parameters.

15. The computing system of claim 14, wherein the plurality of monitors comprises video image capture devices, audio capture devices, pressure sensors, temperature sensors, biometric monitoring devices, monitors configured to log accesses to computing system applications, monitors configured to log participation in computing system or network based games, monitors configured to log accesses to social networking websites, monitors configured to log accesses to non-work related websites or combinations thereof.

16. The computing system of claim 14, wherein data related to real time behavioral attributes comprise heart rate, respiration rate, eye movement, posture, work station ergonomics, length of time sitting, elapsed time on a given task, elapsed time since last break, video data, audio data, visited websites, executed computing programs, executed computing system or networked based games, social networking websites or combinations thereof.

17. The computing system of claim 14, wherein:

the computing system further comprises a cumulative behavioral attribute module in communication with the behavioral attribute analysis module to obtain cumulative historical behavioral attributes for each computing system user; and a cumulative behavioral attribute database to store logs of the cumulative historical behavioral attributes; and the behavioral attribute analysis module determines the aggregate behavioral attribute score for the pre-defined team further based on the log of cumulative historical behavioral attributes for each computing system and the received real time behavioral attributed.

18. The computing system of claim 17, wherein the cumulative historical behavioral attributes comprise habitual exercise routines, preventative health care visits, adherence to prescribed medical treatments, participation in professional meetings, continuing education, work attendance record, employee evaluations, participation in charitable works, attending to family obligations, participation in civic organizations or combinations thereof.

19. The computing system of claim 14, wherein the access control module adjusting access to computing system resources by decreasing allocation of central processor unit power, decreasing available network bandwidth, prohibiting access to computing system applications, prohibiting access to computing system based games, prohibiting access to websites, prohibiting access to social media sites or combinations thereof.

20. The computing system of claim 14, wherein the computing system further comprises:

a computing system resource access monitor in communication with computing system resources to log accesses to computing system applications, accesses to computing system or network based games, accesses to social networking websites and accesses to websites by the computing system users, to identify habitually accessed computing system resources based on frequency and duration of the logged accesses and to create the preferred and habitually accessed computing system resource set associated with the pre-defined team; and a preferred data resource database in communication with the computing system resource monitor and the access control module to store the preferred and habitually accessed computing system resource set.

* * * * *